United States Patent [19]
Zey et al.

[11] Patent Number: 5,344,979
[45] Date of Patent: Sep. 6, 1994

[54] PROCESS FOR PREPARING COLOR-STABILIZED ACETAMINOPHEN

[75] Inventors: Edward G. Zey; George A. Blay, both of Corpus Christi, Tex.

[73] Assignee: Hoechst Celanese Corporation, Somerville, N.J.

[21] Appl. No.: 54,733

[22] Filed: Apr. 29, 1993

[51] Int. Cl.$^5$ ............................................ C07C 231/24
[52] U.S. Cl. ................................... 564/216; 564/144; 564/223
[58] Field of Search ............ 564/216, 223, 144; 568/302; 562/602, 840, 887; 560/130

[56] References Cited

U.S. PATENT DOCUMENTS

| | | | |
|---|---|---|---|
| 2,945,870 | 7/1960 | Young | 564/141 |
| 3,042,719 | 7/1962 | Hahn et al. | 564/216 |
| 3,076,030 | 1/1963 | Freifelder | 564/144 |
| 3,113,150 | 12/1963 | Young | 564/216 |
| 3,748,358 | 7/1973 | Baron | 564/216 |
| 3,781,354 | 12/1973 | Kosak | 564/216 |
| 4,474,985 | 10/1984 | Keel et al. | 564/216 |
| 4,524,217 | 6/1985 | Davenport et al. | 564/223 |
| 4,540,815 | 9/1985 | Papenfuhs et al. | 564/216 |
| 4,954,652 | 9/1990 | Fritch et al. | 564/223 |
| 5,155,273 | 10/1992 | Fritch et al. | 564/223 |

Primary Examiner—Richard L. Raymond
Assistant Examiner—Scott C. Rand
Attorney, Agent, or Firm—James J. Mullen; Donald R. Cassady

[57] ABSTRACT

A method is provided for purifying a crude N-acetyl-para-aminophenol (APAP) containing color bodies or their precursors, the method comprising: a) forming a wet crude APAP; and b) subsequently drying said crude APAP in the presence of a sufficient amount of an acetylating agent for a sufficient period of time to convert said color bodies or their precursors to substantially non-color bodies.

21 Claims, No Drawings

PROCESS FOR PREPARING COLOR-STABILIZED ACETAMINOPHEN

BACKGROUND OF THE INVENTION

1. Field of the Invention

This invention relates to an improved method for the purification of N-acetyl-para-aminophenol (APAP), also known as acetaminophen. APAP is a well-known over-the-counter analgesic and anti-pyretic agent.

2. Description of Related Art

The following prior art references are disclosed in accordance with the terms of 34 CFR 1.56, 1.97, and 1.98.

U.S. Pat. No. 3,042,719, issued Jul. 3, 1962, to Hahn et al., discloses the purification of crude discolored APAP by acidifying an aqueous solution of the APAP with a mineral acid, filtering the solution while hot, and cooling the filtrate while adding an alkaline reducing sulfite, e.g., sodium hydrosulfite (sodium dithionite). A "decolorizing" carbon may be added to the hot solution.

U.S. Pat. No. 3,113,150, issued Dec. 3, 1963, to Young, teaches the preparation of "pure" APAP by reacting mixture to precipitate the APAP, filtering to remove excess acetic acid, neutralizing the wet APAP with ammonium hydroxide, and agitating the resulting solution with carbon black.

U.S. Pat. No. 3,748,358, issued Jul. 24, 1973, to Baron, discloses the purification of APAP by treating it in aqueous solution with carbon which has been preliminarily treated with an acidic solution.

U.S. Pat. No. 3,781,354, issued Dec. 25, 1973, to Kosak, teaches the purification of APAP by treating it in hot aqueous solution with ferric chloride and adsorbing the colored by-product on activated carbon.

U.S. Pat. No. 4,524,217, issued Jun. 18, 1985, to Davenport et al., teaches an integrated process for the production of APAP comprising acetylating phenol by a Friedel-Crafts reaction, or subjecting phenyl acetate to a Fries rearrangement to produce 4-hydroxy-acetophenone (4-HAP), reacting the 4-HAP with hydroxylamine or a hydroxylamine salt to form 4-HAP oxime, and subjecting the latter oxime to a Beckmann rearrangement to form APAP.

All of the aforementioned U.S. patents are incorporated herein by reference, including the entire disclosures thereof.

Additional Background Information

In the manufacture of APAP by any of the known methods, it has been found that there is a tendency for color bodies and color body precursors to form which cause the crude product to have or to develop subsequently an undesirable colored appearance. Because of this, various methods have been developed for the purification of APAP, which remove color bodies in addition to other impurities, such that the purified product has a substantially pure white appearance. These methods often include the addition to a hot aqueous solution of APAP containing color bodies of an adsorbent carbon, which is a well-known decolorizing agent. Some of these methods are described in the disclosures of several of the previously cited references.

It has been found that a disadvantage of decolorizing APAP by contacting a hot aqueous solution of the crude APAP with an adsorbent carbon is that certain impurities appear for the first time or increase as a result of such treatment, which impurities were not present previously, i.e., in the crude APAP before purification. In view of the fact that the main use for APAP is as a pharmaceutical, the presence of these impurities must be kept to a very low practical maximum, either by preventing their formation, or removing the bulk of them subsequent to the carbon treatment, or converting these impurities to substantially non-color bodies.

SUMMARY OF THE INVENTION

In accordance with this invention, a crude APAP containing undesirable color bodies or their precursors is subjected to a purification treatment comprising the steps of forming a wet, but solid, crude APAP, and subsequently drying said crude APAP in the presence of a sufficient amount of an acetylating agent for a sufficient period of time to cause said undesirable color bodies to be converted to non-color bodies or non-color-causing bodies. It has been found that the treatment of the crude APAP with the acetylating agent substantially reduces the undesirable color bodies (impurities) which are observed to form during the preparation of the crude APAP and even at other points in the overall refining stages prior to a final drying step.

DESCRIPTION OF THE PREFERRED EMBODIMENTS

The method of the present invention is useful in the preparation of a relatively pure decolorized APAP, regardless of the manufacturing process used to produce the crude APAP since such method accomplishes the reduction of impurities or undesirable color bodies formed during preparation of the APAP and even at other points in the overall refining stages prior to a final drying step. Thus, the APAP may be produced, for example by the process illustrated in the examples of previously cited U.S. Pat. No. 4,524,217 as summarized in the foregoing description of the disclosure of that patent, or by the previously developed process of reacting para-aminophenol (PAP) with acetic anhydride, as described, for example, in previously cited U.S. Pat. No. 3,113,150.

As previously mentioned in the production of APAP by the herein-described prior art processes, undesirable color bodies or impurities are produced. One of the major impurity components relative to this color stability problem is para-aminophenol (PAP). We have discovered that the addition of small quantities of an acetylating agent during the APAP drying step substantially reduces the PAP levels and thus provides a more color-stable product as measured by a total color index (TCI).

Once the crude APAP is produced by one or more of the prior art processes as described herein, the material can be purified or refined by several processes described in the aforementioned prior art. For example, the crude APAP material can be placed in a separate vessel where it can be dissolved in water. The crude APAP can then be treated with carbon, such as activated carbon, if one so desires to pre-test. However, it was found that undesirable color bodies or impurities are still present, in unacceptable amounts, throughout all of those prior art purification steps. It was unexpectedly found that if a wet (or damp) crude APAP is dried in the presence of an acetylating agent, the undesirable color bodies (impurities), such as PAP, or possible organic derivatives therefrom, are converted to non-offensive materials, i.e. those which do not promote an adverse or undesired color, or in the alternative and at a very minimum, these materials (color bodies) are substantially reduced to acceptable levels, at which the color in the final dried product is controlled and stabilized for normal shelf life of the product.

Drying wet crude APAP can be carried out in any conventional manner known or disclosed in the prior art. For example, such material may be dried by conventional fluidized bed techniques and at temperatures of at least 40° C. Such conditions and/or limitations include the use of an inert gas, such as nitrogen, to provide not only the fluidizing fluid but also the heat to remove the water from the wet APAP. It is also within the scope of this invention to use a movable conveyer belt, which is provided with holes, to pass heated gases through the bed of wet APAP, as means to dry the material.

The acetylating agent used is basically any material which can convert PAP, or possible organic derivatives therefrom, or other organic amines, to APAP or any other chemical which is stable to oxidation and/or polymerization and which will not result in color contamination or adverse color promotion thereof. While it is not desired to be limited by any theory of the invention, it may be postulated that the acetylating agent functions to "tie up" aromatic amines and related color body precursors, and thereby reduce color stability problems. Acetylating agents which fall within this category, and thus can be employed in this invention include (but are not limited to) acetic anhydride, acetic-propionic anhydride, acetyl chloride, phenyl acetate, and ketene.

The amount of acetylating agent used in this drying step is generally less than 2.0% by weight, based on the total weight of the crude APAP being dried. Preferably, the amount is from about 0.001% to 1.5% by weight. It is also within the scope of this invention to use greater than 2.0%, e.g. 2.,0 to 5.0%, if one so desires and if such greater amounts have little or not effect on the desired end product (APAP).

The following examples further illustrate the invention.

EXAMPLES 1–3

A 1500 gm. sample of acetaminophen (APAP) is purified by crystallization from water, such purification involving normal additional purification steps such as carbon treatment, filtration and water washing after filtration. This washed (wet) material is divided into three equal portions and each portion is placed into a fluidized bed dryer. In one experiment the charge of damp (wet) APAP crystals is subjected to fluidized bed drying involving treatment with nitrogen, 55° C., 30 min drying time and a nitrogen flow rate sufficient to fluidize the bed in a 20 liter chamber. The dry material is obtained with the following characteristics:

| | |
|---|---|
| Wt. % Water | 0.53% |
| Total organic impurities | 183 ppm |
| PAP level | 21 ppm |
| APAP Assay | 99.3% |
| Initial Color (IC) | 0.007 |
| Total Color Index (TCI)* | 0.061 |

*Using a Shimodzu UV-160 UV-VIS spectrophotometer

In a second experiment, the second change of wet APAP is charged to the fluidized bed drier and dried in an identical manner, except that after the first minute of drying vaporous acetic anhydride is added at the rate of 1 gram per minute in with the hot nitrogen supply for the next 10 minutes. The normal drying is resumed as described above. The dried APAP material analyzes as follows:

| | |
|---|---|
| Wt. % Water | 0.58% |
| Total organic impurities | 179 ppm |
| PAP level | 12 ppm |
| APAP Assay | 99.2% |
| Initial Color (IC) | 0.005 |
| Total Color Index (TCI) | 0.053 |

In a third experiment, the third charge of wet APAP is charged to the fluidized bed drier and dried in an identical manner, except that after the first minute of drying vaporous acetic anhydride is added at a rate of 2 grams per minute in with the hot nitrogen supply for the next 10 minutes. The normal drying is resumed as described above. The dried APAP analyzes as follows:

| | |
|---|---|
| Wt. % Water | 0.61 |
| Total organic impurities | 176 ppm |
| PAP level | 9 ppm |
| APAP Assay | 99.3% |
| Initial Color (IC) | 0.004 |
| Total Color Index (TCI) | 0.046 |

The three dried samples are subjected to laboratory storage experiments wherein the samples are stored for three weeks. After storage, these samples have the following color characteristics:

| | |
|---|---|
| Sample 1 | 0.019 IC |
| Sample 2 | 0.013 IC |
| Sample 3 | 0.008 IC |

The data above indicate that the PAP levels are reduced in the final product with the acetic anhydride addition. Also, the TCI test of the product involving acetic anhydride treatment indicated a lower value of 0.053 and 0.046. The run without acetic anhydride produced a typical TCI value of 0.061 which is not acceptable.

The initial IC of the run without acetic anhydride is 0.007. The IC values for the runs 2 and 3 with acetic anhydride are 0.005 and 0.004, respectively, and are acceptable.

Total organic impurities were satisfactory. They ranged between 176 to 183 ppm, which is below industry specification limits.

Overall, these results indicate that a high quality APAP product can be produced with regard to using acetic anhydride. This treatment decreases the PAP and TCI levels significantly in the final APAP product.

Based on the above, it can be readily seen that using acetic anhydride in the drying process affords a superior color-stable product.

EXAMPLES 4–7

Examples 1–3 above are repeated using the same conditions as set forth therein with the exception that the acetylating agent is, respectively, acetic-propionic anhydride, acetyl chloride, phenyl acetate, and ketene instead of acetic anhydride. The results are substantially the same as those obtained using acetic anhydride and demonstrate, overall, the preparation of a good color-stable product.

It is also within the scope of the present invention to add the acetylating agent at other process steps during the overall purification procedure. However, it is critical that such acetylating agent be added only after the basic reaction is carried out in preparing the APAP, i.e. downstream of the reaction zone. Thus it falls within the scope of the present invention to employ the acetylating agent at process points such as (1) product filtration, neutralization, and dissolving steps; (2) carbon treating steps; (3) the filter steps for removing carbon; (4) crystallization steps for precipitating APAP crystal solids; (5) centrifuging steps for removing APAP solids from the mother liquor; in addition to the drying step wherein wet APAP is dried to provide a final product.

Thus, in the scope of the present invention, there is provided a method of preparing N-acetyl-para-aminophenol (APAP) which comprises the steps of reacting acetic anhydride with a mixture of p-aminophenol and water, cooling the reaction mixture to precipitate the APAP, filtering to remove excess acid, neutralizing the wet APAP with a basic material such as ammonium hydroxide, and agitating the resulting solution with carbon black, wherein the improvement comprises adding sufficient quantities of an acetylating agent to the crude APAP at any point after the formation of said crude APAP whereby the color bodies or their precursors in said crude APAP will be substantially converted to non-color bodies.

Further in the scope of the present invention, there is provided a process of preparing an N-acyl-hydroxy aromatic amine which comprises the steps of contacting a hydroxy aromatic ketone with a hydroxylamine salt and a base to form the ketoxime of said ketone, and contacting said ketoxime with a Beckmann rearrangement catalyst to form said crude aromatic amine containing color bodies or their precursors, wherein the improvement comprises contacting said crude aromatic amine with an acetylating agent for a sufficient period of time to convert said color bodies or their precursors to substantially non-color bodies.

Also in the scope of the present invention, there is provided a method of preparing N-acetyl-para-aminophenol (APAP) which comprises the steps of reacting 4-hydroxyacetophenone with a hydroxylamine salt and a base to obtain 4-hydroxyacetophenone oxime and then subjecting the 4-hydroxyacetophenone oxime to a Beckmann rearrangement in the presence of a catalyst to form the crude APAP containing color bodies or their precursors wherein the improvement comprises contacting said crude APAP with an acetylating agent for a sufficient period of time to convert said color bodies or their precursors to substantially non-color bodies.

What is claimed is:

1. A method of purifying a crude N-acetyl-para-aminophenol (APAP) containing color bodies or their precursors comprising forming a wet, crude APAP, and subsequently drying said crude APAP in the presence of a sufficient amount of an acetylating agent for a sufficient period of time to convert said color bodies or their precursors to substantially non-color bodies.

2. The method of claim 1 wherein said acetylating agent is acetic-propionic anhydride.

3. The method of claim 1 wherein said acetylating agent is acetyl chloride.

4. The method of claim 1 wherein said acetylating agent is phenyl acetate.

5. The method of claim 1 wherein said acetylating agent is ketene.

6. The method of claim 1 wherein said acetylating agent is acetic anhydride.

7. The method of claim 1 wherein said acetylating agent is present in an amount of from about 0.001% to about 2%, based on the weight of the crude APAP.

8. The process of claim 1 wherein the crude APAP is first treated with carbon and the carbon removed prior to contacting said crude APAP with said acetylating agent.

9. In a method of preparing N-acetyl-para-aminophenol (APAP) which comprises the steps of reacting acetic anhydride with a mixture of p-aminophenol and water, cooling the reaction mixture to precipitate the APAP, filtering to remove excess acetic acid, neutralizing the wet APAP with ammonium hydroxide, and agitating the resulting solution with carbon black, the improvement which comprises adding sufficient quantities of an acetylating agent to the crude APAP at any point after the formation of said crude APAP whereby the color bodies or their precursors in said crude APAP will be substantially converted to non-color bodies.

10. In a process of preparing an N-acyl-hydroxy aromatic amine which comprises the steps of contacting a hydroxy aromatic ketone with a hydroxylamine salt and a base to form the ketoxime of said ketone, and contacting said ketoxime with a Beckmann rearrangement catalyst to form said crude aromatic amine containing color bodies or their precursors, the improvement which comprises contacting said crude aromatic amine with an acetylating agent for a sufficient period of time to convert said color bodies or their precursors to substantially non-color bodies.

11. In a method of preparing N-acetyl-para-aminophenol (APAP) which comprises the steps of reacting 4-hydroxyacetophenone with a hydroxylamine salt and a base to obtain 4-hydroxyacetophenone oxime and then subjecting the 4-hydroxyacetophenone oxime to a Beckmann rearrangement in the presence of a catalyst to form the crude APAP containing color bodies or their precursors, the improvement which comprises contacting said crude APAP with an acetylating agent for a sufficient period of time to convert said color bodies or their precursors to substantially non-color bodies.

12. The method of claim 11 wherein said acetylating agent is acetic-propionic anhydride.

13. The method of claim 11 wherein said acetylating agent is acetyl chloride.

14. The method of claim 11 wherein said acetylating agent is phenyl acetate.

15. The method of claim 11 wherein said acetylating agent is ketene.

16. The method of claim 11 wherein said acetylating agent is acetic anhydride.

17. The method of claim 11 wherein said acetylating agent is present in an amount of from about 0.001% to about 2%, based on the weight of the crude APAP.

18. The method of claim 11 wherein the crude APAP is first treated with carbon and the carbon removed prior to contacting said crude APAP with said acetylating agent.

19. The method of claim 11 wherein the contacting step is carried out in a fluidized bed wherein said crude APAP is dried at a temperature of at least 40° C.

20. The method of claim 19 wherein the fluidized bed is maintained by an inert gas.

21. The method of claim 11 wherein said acetylating agent is present in an amount of from about 0.01% to about 5.0% based on the weight of the crude APAP.

* * * * *